US006680403B1

(12) United States Patent
Ionkin et al.

(10) Patent No.: US 6,680,403 B1
(45) Date of Patent: Jan. 20, 2004

(54) PROCESS FOR HYDROGENATING DINITRILES IN AMINONITRILES

(75) Inventors: Alex Sergey Ionkin, Newark, DE (US); Stanislaw Bodgan Ziemecki, Wilmington, DE (US); Mark J. Harper, Lewes, DE (US); Theodore Augur Koch, Wilmington, DE (US); Henry Edward Bryndza, Avondale, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/030,369

(22) PCT Filed: Apr. 25, 2000

(86) PCT No.: PCT/US00/11045
§ 371 (c)(1),
(2), (4) Date: Oct. 25, 2001

(87) PCT Pub. No.: WO00/64862
PCT Pub. Date: Nov. 2, 2000

Related U.S. Application Data

(60) Provisional application No. 60/188,664, filed on Mar. 10, 2000, provisional application No. 60/188,661, filed on Mar. 10, 2000, provisional application No. 60/188,289, filed on Mar. 8, 2000, provisional application No. 60/194,248, filed on Apr. 3, 2000, provisional application No. 60/174,998, filed on Jan. 7, 2000, and provisional application No. 60/168,035, filed on Nov. 30, 1999.

(51) Int. Cl.$^7$ ............................................. C07C 255/04
(52) U.S. Cl. ...................................................... 558/459
(58) Field of Search ................................. 558/452, 459; 502/150

(56) References Cited

U.S. PATENT DOCUMENTS

| 2,208,598 | A | 7/1940 | Rigby |
| 2,257,814 | A | 1/1941 | Rigby |
| 2,245,129 | A | 6/1941 | Greenewalt |
| 2,762,835 | A | 9/1956 | Swerdloff |
| 3,322,815 | A | 5/1967 | Feldman et al. |
| 3,350,439 | A | 10/1967 | Feldman et al. |
| 3,591,618 | A | 7/1971 | Hanschke et al. |
| 4,248,799 | A | 2/1981 | Drake |
| 4,389,348 | A | 6/1983 | Diamond et al. |
| 4,472,529 | A | 9/1984 | Johnson et al. |
| 4,499,204 | A | 2/1985 | Vanderspurt et al. |
| 4,568,736 | A | 2/1986 | Curatolo et al. |
| 4,601,859 | A | 7/1986 | Galle et al. |
| 5,151,543 | A | 9/1992 | Ziemecki |
| 5,296,628 | A | 3/1994 | Sanchez |
| 5,512,697 | A | 4/1996 | Schnurr et al. |
| 5,527,946 | A | 6/1996 | Flick et al. |
| 5,986,127 | A | * 11/1999 | Ionkin et al. ............... 558/459 |
| 6,011,179 | A | 1/2000 | Haas et al. |

FOREIGN PATENT DOCUMENTS

| DE | 836 938 | | 4/1952 |
| DE | 848 654 | | 9/1952 |
| DE | 19636768 A1 | | 3/1998 |
| GB | 2 114 974 A | * | 9/1983 |
| JP | 6182203 A | | 5/1994 |
| JP | 9-40630 | * | 2/1997 |
| JP | 9040630 A | | 10/1997 |
| WO | WO 99/47492 | | 9/1999 |

OTHER PUBLICATIONS

Mares et al., Preparation and Characterization of a Novel Catalyst for the Hydrogenation of Dinitriles to Aminonitriles, Journal of Catalysis, 112, 145–156, Apr. 20, 1987; revised Nov. 3, 1987.

Szilagyi, Tibor, Infrared spectra of methyl cyanide and methyl isocyanide adsorbed on platinum/silica, retrieved from STN, Database accession No. 110:64225—XP002152565 abstract, Appl. Surf. Sci. (1988), 35(1), 19–26.

* cited by examiner

Primary Examiner—Sreeni Padmanabhan
Assistant Examiner—Ebenezer Sackey
(74) Attorney, Agent, or Firm—Bart E. Lerman

(57) ABSTRACT

Provided is a selective hydrogenation process for producing aminonitriles by contacting the corresponding dinitriles with a hydrogen-containing fluid in the presence of a hydrogenation catalyst, a solvent and an additive for improving the yield of and/or selectivity to the aminonitrile. The additive comprises a carbon monoxide; a tetraalkylammonium hydroxide compound; a tetraalkylphosphonium hydroxide compound; a multi-centered metal carbonyl cluster; an organic isonitrile; a cyanide compound having at least one cyano group bound to other than a carbon atom; and afluoride compound.

17 Claims, No Drawings

PROCESS FOR HYDROGENATING DINITRILES IN AMINONITRILES

This application is a 371 of PCT/US00/11045 filed Apr. 25, 2000 which claims benefit of Ser. No. 60/168,035, filed Nov. 30, 1999 which claims benefit of Ser. No. 60/194,248, filed Apr. 3, 2000 which claims benefit of Ser. No. 60/188,289, filed Mar. 8, 2000 which claims benefit of Ser. No. 60/188,661, filed Mar. 3, 2000 which claims benefit of Ser. No. 60/188,664 filed Mar. 10, 2000 and Ser. No. 60/174,998 filed Jan. 7, 2000.

FIELD OF THE INVENTION

The invention relates to a selective hydrogenation process for producing aminonitriles from corresponding dinitriles in the presence of one or more additives that improve the yield of and/or selectivity to the aminonitrile.

BACKGROUND OF THE INVENTION

Aminonitriles are a class of important chemicals that have a variety of industrial applications. For example, aminonitriles can be used as monomers for producing high molecular weight polyamides. Specifically, 6-aminocapronitrile can be used to produce nylon 6.

Aminonitriles can be produced by catalytic partial hydrogenation of dinitriles. See, for example, U.S. Pat. No. 2,208,598, U.S. Pat. No. 2,257,814, U.S. Pat. No. 2,762,835, U.S. Pat. No. 3,322,815, U.S. Pat. No. 3,350,439, U.S. Pat. No. 3,591,618, U.S. Pat. No. 4,389,348, U.S. Pat. No. 4,601,859, U.S. Pat. No. 5,151,543, U.S. Pat. No. 5,296,628, U.S. Pat. No. 5,512,697, U.S. Pat. No. 5,527,946, DE836938, DE848654, DE-A-19636768 and WO99/47492, all of which are incorporated by reference herein for all purposes as if fully set forth. However, the yield of and selectivity to a desired aminonitrile using some of the known processes may not be as high as desired, and the amount of the complete hydrogenation product (diamine) is also generally higher than desired.

WO99/47492 mentioned above describes the use of certain carbonyl group-containing compounds as additives in the partial hydrogenation process to improve the yield of and/or selectivity to the desired aminonitrile product, and/or reduce the amount of fully hydrogenated product (diamine) produced.

We have now found new classes of compounds that also effectively function as improved yield and/or selectivity additives in the partial hydrogenation processes such as, for example, those mentioned in previously incorporated WO99/47492.

SUMMARY OF THE INVENTION

In accordance with one aspect of the present invention, there is provided a process for the partial hydrogenation of a dinitrile to an aminonitrile, comprising the step of contacting the dinitrile with a hydrogen-containing fluid in the presence of (a) a solvent comprising liquid ammonia, an alcohol, or both; (b) a hydrogenation catalyst; and (c) an additive for improving the yield of and/or selectivity to the aminonitrile, characterized in that the additive comprises a compound selected from the group consisting of:

carbon monoxide;
a tetraalkylammonium hydroxide compound;
a tetraalkylphosphonium hydroxide compound;
a multi-centered metal carbonyl cluster;
an organic isonitrile;
a cyanide compound having at least one cyano group bound to other than a carbon atom; and
a fluoride compound.

Another aspect of the present invention relates to a process for improving the yield of and/or selectivity to an aminonitrile obtained by partially hydrogenating a corresponding dinitrile with a hydrogen-containing fluid in the presence of a solvent and a hydrogenation catalyst, comprising the step of partially hydrogenating the dinitrile in the further presence of an effective amount of an additive comprising a compound selected from the group consisting of:

carbon monoxide;
a tetraalkylammonium hydroxide compound;
a tetraalkylphosphonium hydroxide compound;
a multi-centered metal carbonyl cluster;
an organic isonitrile;
a cyanide compound having at least one cyano group bound to other than a carbon atom; and
a fluoride compound.

In yet another aspect of the present invention, there is provided a catalyst composition comprising a combination of (1) a hydrogenation catalyst suitable for hydrogenating a dinitrile to an aminonitrile; and (2) an additive that improves the yield of and/or selectivity to the aminonitrile from said catalyst under hydrogenation conditions, characterized in that the additive comprises a compound selected from the group consisting of:

carbon monoxide;
a tetraalkylammonium hydroxide compound;
a tetraalkylphosphonium hydroxide compound;
a multi-centered metal carbonyl cluster;
an organic isonitrile;
a cyanide compound having at least one cyano group bound to other than a carbon atom; and
a fluoride compound.

An advantage of this invention is that an aminonitrile can be produced in higher yield and/or having a higher selectivity to the aminonitrile with the additive than without. Other objects and advantages will become more apparent as the invention is more fully disclosed herein below.

DETAILED DESCRIPTION OF THE PREFERRED EMBODIMENTS

According to this invention, a dinitrile is contacted with a hydrogen-containing fluid in the presence of a solvent, a catalyst and an additive as generally described above.

Suitable dinitriles for use herein have the general formula $R(CN)_2$, wherein R is a hydrocarbylene group selected from the group consisting of an alkylene, arylene, alkenylene, alkarylene and aralkylene group. One dinitrile or combinations of different dinitriles may be used. Preferred hydrocarbylene groups contain from 2 to 25, more preferably 2 to 15, and most preferably 2 to 10 carbon atoms per group. In other words, preferred dinitriles contain from 4 to 27, more preferably 4 to about 17, and most preferably 4 to 12, carbon atoms per dinitrile molecule. The preferred type of hydrocarbylene group is an alkylene group.

Examples of suitable dinitriles include, but are not limited to, adiponitrile; methylglutaronitrile; alpha,omega-pentanedinitrile; alpha,omega-heptanedinitrile; alpha, omega-nonanedinitrile; alpha, omega-dodecanedinitrile;

alpha, omega-pentadecanedinitrile; alpha,omega-icosanedinitrile; alpha,omega-tetracosane-dinitrile; 3-methylhexanedinitrile; 2-methyl-4-methyleneoctanedinitrile; and combinations of two or more thereof.

Preferably the carbon atoms of the starting dinitrile are arranged in a branched or linear chain. Preferred examples are adiponitrile (hydrogenated to 6-aminocapronitrile), methylglutaronitrile (hydrogenated to two isomeric aminonitriles: 5-amino-2-methylvaleronitrile and 5-amino-4-methyl-valeronitrile) and alpha,omega-dodecanedinitrile (hydrogenated to the corresponding aminonitrile). The preferred dinitrile is adiponitrile because its selective hydrogenation product, 6-aminocapronitrile, is a well-known monomer for polymerization applications.

Any hydrogen-containing fluid can be used in the invention as long as there is sufficient hydrogen in the fluid to selectively hydrogenate a dinitrile to an aminonitrile. The term "fluid" refers to liquid, gas or both. The hydrogen content in the fluid can range from 1 to 100%, preferably about 50 to about 100%, and most preferably 90 to 100% by volume. The presently preferred hydrogen-containing fluid is substantially pure hydrogen gas.

The molar ratio of hydrogen (in the hydrogen-containing fluid) to dinitrile is not critical as long as sufficient hydrogen is present to produce the desired aminonitrile. Hydrogen is generally used in excess. Hydrogen pressures are generally in the range of about 50 to about 2000 psig (about 0.45 to about 13.89 MPa), with from about 200 to about 1000 psig (about 1.48 to about 7.00 MPa) preferred.

It should be noted that, unless otherwise indicated, pressures expressed as "psi" are gauge pressures (e.g., psig), and pressures expressed as "MPa" are absolute pressures.

Any solvent that comprises either liquid ammonia or an alcohol can be used in the invention. The concentration of liquid ammonia in the solvent can range from about 20 to about 100%, preferably about 50 to about 100%, and most preferably about 80% to about 100%, by weight of total solvent. A substantially pure liquid ammonia is preferred. However, if an alcohol is also present in the solvent, the concentration of ammonia can be adjusted based on the quantity of alcohol used, which is discussed in further detail below. The molar ratio of ammonia to dinitrile is preferably about 1:1 or greater, and is generally in the range of from about 1:1 to about 30:1, more preferably from about 2:1 to about 20:1.

Any alcohol that can facilitate the selected hydrogenation of a dinitrile to an aminonitrile can be used in this invention. Preferred are alcohols with 1 to 10, more preferably 1 to 4, carbon atoms per molecule. Examples of suitable alcohols include, but are not limited to, methanol, ethanol, propanol, isopropyl alcohol, butanol, isobutyl alcohol, pentanol, hexanol, heptanol, octanol, nonanol, decanol, and combinations of two or more thereof. The most referred alcohol (when used) is methanol. The alcohol can enerally be present in the solvent in the concentration of from about 20 to about 100%, preferably about 30 to about 99%, by weight based on the total solvent weight.

Typically when an alcohol is use, the solvent further comprises a base that is substantially soluble in the solvent. The term "substantially" refers to "more than trivial". Preferred bases are ammonia, an ammonium base or an inorganic base such as, for example, alkali metal oxides, alkaline earth metal oxides, alkali metal hydroxides, alkaline earth metal hydroxides, partially neutralized acids in which one or more protons of the acids are replaced with ammonium ion, alkali metal ions, alkaline earth metal ions, or combinations of two or more thereof. Specific examples of suitable bases include, but are not limited to ammonia, lithium hydroxide, sodium hydroxide, potassium hydroxide, sodium bicarbonate, sodium carbonate, potassium bicarbonate, or combinations of two or more thereof. The most preferred bases are ammonia, lithium hydroxide and sodium hydroxide for they are readily available and inexpensive.

A base can be present in the solvent in any quantity so long as the quantity can facilitate the selective hydrogenation of a dinitrile to an aminonitrile. Generally, a base can be present in the solvent in the range of from about 0.1 to about 10 weight %, based on the total weight of the starting dinitrile.

The catalyst in the process is a hydrogenation catalyst suitable for hydrogenating a dinitrile to an aminonitrile. Preferred are catalysts based on transition metals selected from the group consisting of iron, cobalt, nickel, rhodium and combinations thereof. The catalyst may also contain one or more promoters in addition to the transition metals mentioned above, for example, one or more of Group VIB and Group VII metals such as chromium, molybdenum and tungsten. The catalyst can also be in the form of an alloy, including a solid solution of two or more metals, or an individual metal.

The catalytic metal can also be supported on an inorganic support such as alumina, magnesium oxide and combinations thereof. The metal can be supported on an inorganic support by any means known to one skilled in the art such as, for example, impregnation, coprecipitation, ion exchange, and combinations of two or more thereof. The preferred inorganic support is magnesium oxide, and the preferred supported catalyst is a magnesium oxide supported nickel-iron catalyst.

The catalyst can be present in any appropriate physical shape or form. It can be in fluidizable forms, extrudates, tablets, spheres or combinations of two or more thereof. The catalyst may be in sponge metal form, for example, the Raney® nickels and Raney® cobalts. The molar ratio of catalyst to dinitrile can be any ratio as long as the ratio can catalyze the selective hydrogenation of a dinitrile. The weight ratio of catalyst to dinitrile is generally in the range of from about 0.0001:1 to about 1:1, preferably about 0.001:1 to about 0.5:1. If the catalytic metal is supported on an inorganic support or is a portion of alloy or solid solution, the catalytic metal is generally present in the range of from about 0.1 to about 60, preferably about 1 to about 50, and most preferably about 2 to about 50 weight %, based on the total catalyst weight.

The preferred catalyst is a sponge metal type catalyst. The metallic component is iron, cobalt, nickel or combinations thereof. Commercially available catalysts of this type are promoted or unpromoted Raney® Ni or Raney® Co catalysts that can be obtained from the Grace Chemical Co. (Columbia, Md.), or alternative sponge metal catalysts available, for example, from Activated Metals Corporation (Sevierville, Tenn.) or Degussa (Ridgefield Park, N.J.).

In the case of the supported nickel/iron catalyst, the rate of adiponitrile conversion increases with the amount of Ni deposited on the support. The preferred concentration of Ni is between about 5 and about 50 weight %, and especially between about 25 and about 35 weight %, based on the catalyst weight (metals +support). The preferred concentration of Fe is between about 0.2 and about 20 weight %, and especially between about 0.5 and about 10 weight %, based on the catalyst weight (metals+support).

Further details on the above components can be found from various of the previously incorporated references.

Specific reference may be had, for example, to U.S. Pat. No. 2,208,598, U.S. Pat. No. 2,257,814, U.S. Pat. No. 2,762,835, U.S. Pat. No. 3,322,815, U.S. Pat. No. 5,151,543, U.S. Pat. No. 5,296,628, U.S. Pat. No. 5,512,697, U.S. Pat. No. 5,527,946 and WO99/47492.

Any additive comprising one or more of the above-mentioned compounds that can effect selectivity improvement is useful in the present invention.

The term "improvement" is referred to as enhanced selectivity to aminonitrile product at conversions greater than about 70%, preferably conversions greater than about 80%, and especially conversions greater than about 90%, as compared to the selectivity without the use of the additive of this invention. An "effective amount" of the additive is amount required to achieve the aforementioned enhanced selectivity and/or an improved overall yield of aminonitrile, as compared to without the use of the additive.

In preferred embodiments, the additive consists essentially of one or more of the above-mentioned compounds.

In preferred embodiments, the alkyl groups of the tetraalkylammonium and tetraalkylphosphonium hydroxide compounds each individually contain from 1 to 8 carbon atoms, and more preferably 1–4 carbon atoms. It is preferred that all four of the alkyl groups in a molecule are the same, but mixtures having different tetraalkyl substituents are suitable for use herein.

Examples of suitable tetraalkylammonium hydroxide and tetraalkylphosphonium hydroxide compounds include, but are not limited to, tetramethylammonium hydroxide, tetraethylammonium hydroxide, tetrapropylammonium hydroxide, tetrabutylammonium hydroxide and tetrabutylphosphonium hydroxide.

As indicated above, combinations of two or more tetraalkylammonium hydroxide and/or tetraalkylphosphonium hydroxide compounds are also suitable.

It should be noted that various hydrated forms such as, for example, tetramethylammonium hydroxide pentahydrate, are included within the meaning of tetraalkylammonium hydroxide and tetraalkylphosphonium hydroxide.

By "multi-centered metal carbonyl cluster" is meant a medium to high nuclearity metal carbonyl cluster in which bulk metal properties begin to appear, requiring (i) at least two metal atoms within the cluster, (ii) at least three bridges between the metal atoms within the cluster, and (iii) at least one carbonyl group bonded to a metal atom. As examples of bridges within the cluster may be mentioned metal-metal bonds and bridging groups such as carbonyl groups bonded to two metal atoms. Other suitable bridging groups include, for example, phosphine, arsine and mercapto groups. Group VIIb and Group VIII metals are preferred; particularly iron, cobalt, ruthenium, rhodium, osmium, rhenium and iridium; and especially the Group VIII metals iron, ruthenium, rhodium and osmium. In addition to the metal atoms and bridges, the multi-centered metal carbonyl clusters may contain a wide variety of other peripheral moieties such as, for example, cyclopentadienyl groups.

Examples of suitable multi-centered metal carbonyl clusters include, but are not limited to, iron nonacarbonyl—$Fe_2(CO)_9$, cyclopentadienyliron dicarbonyl dimer—$[Cp_2Fe(CO)_2]_2$, tetracobalt dodecacarbonyl—$Co_4(CO)_{12}$, ruthenium carbonyl—$Ru_3(CO)_{12}$, hexarhodium hexadecacarbonyl—$Rh_6(CO)_{16}$, osmium carbonyl—$Os_3(CO)_{12}$, iridium carbonyl—$Ir_4(CO)_{12}$, rhenium carbonyl—$Re_2(CO)_{10}$. Preferred of the above are iron nonacarbonyl, ruthenium carbonyl, hexarhodium hexadecacarbonyl and osmium carbonyl. Combinations of multi-centered metal carbonyl clusters may also be used.

Preferred organic isonitriles are those of the general formula R'—N≡C:, where R' is a hydrocarbyl group (such as an alkyl, aryl or aralkyl group) preferably containing from 1 to 20 carbon atoms, and more preferably from 1 to 10 carbon atoms. Specific examples of suitable organic isonitriles include, but are not limited to, tert-octyl isonitrile (1,1,3,3-tetramethylbutyl isocyanide), tert-butyl isonitrile, n-butyl isonitrile, i-propyl isonitrile, benzyl isonitrile, ethyl isonitrile, amyl isonitrile and methyl isonitrile. Combinations of two or more isonitriles may also be used.

By "cyanide compound" is meant a compound containing at least one cyano group bound to other than a carbon atom. This can include, for example, inorganic cyanides, organic-inorganic cyanides, various salts and/or complexes thereof, and combinations of two or more thereof.

Examples of suitable inorganic cyanides include, but are not limited to, hydrogen cyanide—HCN; metal cyanides such as lithium cyanide—LiCN, sodium cyanide—NaCN, potassium cyanide—KCN, zinc cyanide—$Zn(CN)_2$, copper cyanide—CuCN, and gold cyanide—AuCN; metal-cyano complexes such as potassium hexacyanoferrate (III)—$K_3[Fe(CN)_6]$, potassium hexacyanoferrate (II)—$K_4[Fe(CN)_4]$, potassium hexacyanoco-baltate (III)—$K_3[Co(CN)_6]$, potassium hexacyanoplatinate (IV)—$K_2[Pt(CN)_6]$, and potassium hexacyanoruthenate (II)—$K_4[Ru(CN)_6]$; and inorganic thiocyanides. As examples of inorganic thiocyanides may be mentioned ammonium thiocyanide—$H_4NSCN$, and metal thiocyanides such as sodium thiocyanide—NaSCN, and lithium thiocyanide—LiSCN.

Examples of suitable organic-inorganic cyanides include, but are not limited to, tetraalkylammonium cyanides such as tetrabutylammonium cyanide—$Bu_4NCN$, and tetraethylammonium cyanide—$Et_4NCN$; trialkylsilyl cyanides such as trimethylsilyl cyanide—$(CH_3)_3SiCN$; organic thiocyanides (in which a carbon is attached to the sulfur) and organic-inorganic thiocyanides. As examples of organic-inorganic thiocyanides may be mentioned tetraalkylammonium thiocyanides such as tetramethylammonium thiocyanide—$Me_4NSCN$, tetraethylammonium thiocyanide—$Et_4NSCN$, tetrapropylammonium thiocyanide—$Pr_4NSCN$, and tetrabutylammonium thiocyanide—$Bu_4NSCN$.

Preferred among the cyanide compounds are hydrogen cyanide, the metal cyanides and the thiocyanides.

Examples of suitable fluoride compounds include both organic and inorganic fluoride compounds such as, for example, tetramethylammonium fluoride, tetraethylammonium fluoride, tetrapropylammonium fluoride, tetrabutylammonium fluoride, sodium fluoride, lithium fluoride, diisopropylethylamine trihydrof luoride, diisopropylamine dihydrof luoride, cerium titanium fluoride, hydrogen fluoride/melamine (80% HF), 1,3-dimethylimidazolidinone hexahydrofluoride, poly-4-vinylpyridinium poly(hydrogen fluoride), benzyltrimethylammonium fluoride hydrate, antimony fluoride, potassium hexafluoronickelate(IV), potassium fluoride, triethylamine trihydrofluoride, tetraoctylammonium fluoride, hydrogen fluoride, tetraethylammonium fluoride dihydrate, tetrabutylammonium fluoride trihydrate, hydrogen fluoride 2,4,6-trimethylpyridine, pyridinium poly (hydrogen fluoride), tetramethylammonium fluoride tetrahydrate, hydrazinium difluoride, ammonium hexafluorophosphate fluoride, boron trifluoride-dipropionic acid complex and boron fluoride-acetic acid complex. Preferred of the above are the amine and ammonium fluorides mentioned above as well as the hydrates thereof.

The additive is present during the contacting in any quantity that can improve the selective hydrogenation of a dinitrile to its corresponding aminonitrile (e.g., an effective amount).

For carbon monoxide, the preferred ratio of carbon monoxide to the catalyst is in the range of from about 0.001:1 to about 10:1, preferably about 0.005:1 to about 5:1, and especially about 0.01:1 to about 2:1, mmoles CO/g catalyst.

For the tetraalkylammonium and tertaalkylphosphonium hydroxides, the preferred weight ratio of additive to the catalyst is in the range of from about 0.001:1 to about 2:1, preferably about 0.005:1 to about 1:1, and especially about 0.01:1 to about 0.5:1. If the additive is used in hydrated form, this weight ratio is based on the non-hydrated tetraalkylammonium and/or tetraalkylphosphonium hydroxide compound form.

For the multi-centered metal carbonyl clusters, the preferred weight ratio of additive to the catalyst is in the range of from about 0.001:1 to about 0.5:1, preferably about 0.005:1 to about 0.33:1, and especially about 0.01:1 to about 0.25:1.

For the organic isonitriles, the preferred weight ratio of additive to the catalyst is in the range of from about 0.001:1 to about 2:1, preferably about 0.005:1 to about 1.5:1, and especially about 0.01:1 to about 1:1.

For the cyanide compounds, the preferred weight ratio of additive to the catalyst is in the range of from about 0.001:1 to about 0.5:1, preferably about 0.005:1 to about 0.33:1, and especially about 0.01:1 to about 0.25:1.

For the fluoride compounds, the preferred weight ratio of additive to the catalyst is in the range of from about 0.001:1 to about 1:1, preferably about 0.005:1 to about 0.5:1, and especially about 0.01:1 to about 0.25:1.

The catalyst and additive can be separately introduced into contact with a dinitrile; however, it is preferred that the catalyst, whether it is in its metal form or in an alloy or solid solution or on an inorganic support, is pretreated by contacting with the additive. This may be done in a solvent such as, for example, an alcohol, ether, ester, ammonia or combinations of two or more thereof. Further preferably the precontacting is also carried out in a hydrogen-containing fluid such as described above. Contacting of the catalyst and additive produces a pretreated catalyst. The pretreated catalyst can be washed with a solvent disclosed above, preferably under anaerobic condition to produce an additive-treated catalyst.

The contacting of the catalyst and additive can be carried out under any conditions effective to produce an additive-treated catalyst that can improve selective hydrogenation of a dinitrile or the selectivity to an aminonitrile. Generally, the entire process for producing the additive-treated catalyst can be carried out by contacting a catalyst with an additive disclosed above at a temperature in the range of from about 20° C. to about 150° C., preferably about 30° C. to about 100° C., under the same general pressures as described above, for about 5 seconds to about 25 hours.

For carbon monoxide, the preferred ratio of additive to catalyst in the pre-treating procedure generally ranges from about 0.001:1 to about 10:1, preferably from about 0.005:1 to about 5:1, and more preferably from about 0.01:1 to about 2:1, mmoles CO/g catalyst.

For the tetraalkylammonium and tertaalkylphosphonium hydroxides, the preferred weight ratio of additive to the catalyst in the pre-treating procedure generally ranges from about 0.01:1 to about 5:1, preferably about 0.05:1 to about 3:1, more preferably from about 0.1:1 to about 2:1, and especially about 0.25:1 to about 1:1.

For the multi-centered metal carbonyl clusters, the preferred weight ratio of additive to the catalyst in the pretreating procedure generally ranges from about 0.001:1 to about 0.5:1, preferably about 0.005:1 to about 0.33:1, and especially about 0.01:1 to about 0.25:1.

For the organic isonitriles, the preferred weight ratio of additive to the catalyst in the pre-treating procedure generally ranges from about 0.001:1 to about 2:1, preferably about 0.005:1 to about 1.5:1, and especially about 0.01:1 to about 1:1.

For the cyanide compounds, the preferred weight ratio of additive to the catalyst in the pre-treating procedure generally ranges from about 0.001:1 to about 0.5:1, preferably about 0.005:1 to about 0.33:1, and especially about 0.01:1 to about 0.25:1.

For the fluoride compounds, the preferred weight ratio of additive to the catalyst in the pre-treating procedure generally ranges from about 0.001:1 to about 1:1, preferably about 0.005:1 to about 0.5:1, and especially about 0.01:1 to about 0.25:1.

The partial hydrogenation process of the present invention can be carried out at a temperature in the range of from about 25 to about 150° C., preferably about 40 to about 100° C., most preferably about 60 to about 80° C., at a total pressure generally in the range of about 50 to about 2000 psig (about 0.45 to about 13.89 MPa), with from about 200 to about 1000 psig (about 1.48 to about 7.00 MPa) preferred, for a time period generally in the range of from about 15 minutes to about 25 hours, preferably about 1 hour to about 10 hours.

The process of the invention can be operated batch wise or continuously in an appropriate reactor. Stirring or agitation of the reaction mixture can be accomplished in a variety of ways known to those skilled in the art. The partial hydrogenation of the starting dinitrile to its corresponding aminonitrile with high selectivity at high conversions of the dinitrile makes this process efficient and useful.

Further general and specific process details can be found from various of the previously incorporated references. Specific reference may be had, for example, to U.S. Pat. No. 2,208,598, U.S. Pat. No. 2,257,814, U.S. Pat. No. 2,762,835, U.S. Pat. No. 3,322,815, U.S. Pat. No. 5,151,543, U.S. Pat. No. 5,296,628, U.S. Pat. No. 5,5126,97, U.S. Pat. No. 5,527,946 and WO99/47492.

The following examples further illustrate the process of the invention and are not to be construed to unduly limit the scope of the invention.

The meaning of terms used in the Examples is defined as follows:

Yield of aminonitrile is the measured concentration of aminonitrile divided by the starting concentration of dinitrile.

Conversion of the dinitrile is the difference between the starting and the instant concentration of dinitrile, divided by the starting concentration of dinitrile.

Selectivity to aminonitrile is the measured yield of aminonitrile divided by conversion of the dinitrile at that instance.

Where the use of hydrocyanic acid (hydrogen cyanide) is indicated, it was used as a condensed liquidsmeasured in pre-chilled equipment to minimize evaporative losses.

COMPARATIVE EXAMPLE 1

A sponge Ni catalyst (1.2 g) promoted with Fe and Cr (Activated Metals, A4000, without any further additives) was added to a 50 cc autoclave together with 3.2 g adiponitrile (ADN) and 35 cc of liquid ammonia to form a mixture. Hydrogen was introduced to the autoclave and the ADN was hydrogenated at 60° C. under the total pressure of 1045 psig (7.31 MPa) at ca. 1500 rpm. Total conversion of ADN was reached within 30 minutes on stream. The maximum yield of aminocapronitrile was 57% at 90% ADN conversion for a selectivitiy of 63%.

COMPARATIVE EXAMPLE 2

To a 300 cc autoclave, was charged 7.7 g Raney® Co (obtained from W.R. Grace Co., catalog number 2724), 0.77 g water, 26 g ADN, and 139 g liquid ammonia.

The content was hydrogenated at 70° C., under the total pressure of 1000 psig (7.00 MPa) at 1000 rpm. Total conversion of ADN was reached within 40 minutes on stream. The maximum yield of aminocapronitrile was 58% at 90% ADN conversion for a selectivity of 64%.

COMPARATIVE EXAMPLE 3

To a 50 cc autoclave, was charged 1.2 g of a 5% rhodium on alumina catalyst (obtained from Engelhard), 3.2 g ADN, and 35 ml liquid ammonia. The content was hydrogenated at 80° C., under the total pressure of 1060 psig (7.41 MPa), at 1500 rpm. Total conversion of AND was reached within 30 minutes on stream. The maximum yield of aminocapronitrile was 3% at 96% ADN conversion, with the major product being hexamethylene diamine.

EXAMPLE 1

10.0 g of sponge Ni catalyst (Degussa BLM 112W) was charged into a 50 cc autoclave, together with 1.0 ml of gaseous carbon monoxide under 60 psi of pressure (0.018 mmoles CO per g catalyst) Subsequently, 35 ml of liquid ammonia was added, and the mixture was heated to 80° C. with stirring. The pressure was adjusted to 1000 psig (7.00 Mpa) with hydrogen, then kept under such conditions for 2.5 hrs. After cooling, the pressure was released and the sample was transferred to a dry box, washed with deaerated methanol, and stored under anaerobic conditions. 1.2 g of the sponge Ni catalyst, pretreated with carbon monoxide as described above, was charged into a 50 cc autoclave together with 3.2 g of ADN and 35 ml of liquid ammonia, heated to 60° C., and reacted with hydrogen at a total pressure of 1000 psig (7.00 MPa). After 75 minutes, the yield of 6-aminocapronitrile reached ca. 72% at 94% ADN conversion for a selectivity of 77%.

EXAMPLE 2

1.2 g of the sponge Ni catalyst, pretreated with carbon monoxide, as described in Example 1, was charged into a 50 cc autoclave together with 3.2 g of ADN and 35 ml of liquid ammonia, heated to 40° C., and reacted with hydrogen at a total pressure of 1000 psig (7.00 MPa). After 180 minutes, the yield of 6-aminocapronitrile reached ca. 72% at 93% ADN conversion for a selectivity of 77%.

EXAMPLE 3

A 50 cc autoclave was charged with 3.2 g of ADN, 1.2 g of Raney® Ni, 0.25 g of NaOH, 0.25 g of $H_2O$, 35 ml of MeOH and 6.42 ml of gaseous carbon monoxide under 40 psi pressure (0.077 mmoles CO per g catalyst). The mixture was heated to 70° C., then brought in contact with hydrogen for a total pressure of 500 psig (3.55 MPa), and run for 5 hours. After 4.5 hours, the yield of 6-aminocapronitrile reached ca. 63% at 78% ADN conversion for a selectivity of 81%.

EXAMPLE 4

10.0 g of Raney® Co (W.R. Grace) was charged into a 50 cc autoclave, together with 2.5 ml of gaseous carbon monoxide under 60 psi of pressure (0.045 mmoles CO per g catalyst). Subsequently, 35 ml of liquid ammonia was added, and the mixture was heated to 800C with stirring. The pressure was adjusted to 1000 psig (7.00 Mpa) with hydrogen, then kept under such conditions for 2.5 hrs. After cooling, the pressure was released and the sample was transferred to a dry box, washed with deaerated methanol, and stored under anaerobic conditions. 1.2 g of the Raney® Co catalyst, pretreated with carbon monoxide as described above, was charged into a 50 cc autoclave together with 3.2 g of ADN and 35 ml of liquid ammonia, heated to 40° C., and reacted with hydrogen at a total pressure of 1000 psig (7.00 MPa). After 160 minutes, the yield of 6-aminocapronitrile reached ca. 71% at 89% ADN conversion for a selectivity of 80%.

EXAMPLE 5

10.0 g of Raney® Co (W.R. Grace) was charged into a 50 cc autoclave together with 5.0 ml of gaseous carbon monoxide under 80 psi of pressure (0.12 mmoles CO per g catalyst). Subsequently, 35 ml of liquid ammonia was added, and the mixture was heated to 80° C. with stirring. The pressure was adjusted to 1000 psig (7.00 Mpa) with hydrogen, then kept under such conditions for 2.5 hrs. After cooling, the pressure was released and the sample was transferred to a dry box, washed with deaerated methanol, and stored under anaerobic conditions. 1.2 g of the Raney® Co catalyst, pretreated with carbon monoxide as described above, was charged into a 50 cc autoclave together with 3.2 g of ADN and 35 ml of liquid ammonia, heated to 80° C., and reacted with hydrogen at a total pressure of 1000 psig (7.00 MPa). After 5 hours, the yield of 6-aminocapronitrile reached ca. 74% at 94% ADN conversion for a selectivity of 79%.

EXAMPLE 6

1.2 g of sponge Ni catalyst (Degussa BLM 112W) was charged into a 50 cc autoclave, together with 2.0 g of tetramethylammonium hydroxide pentahydrate. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C. , and reacted with hydrogen at a total pressure of 1000 psig (7.00 MPa). After 24 minutes, the yield of 6-aminocapronitrile reached ca. 79% at 97% ADN conversion for a selectivity of 81%.

EXAMPLE 7

1.2 g of sponge Ni catalyst (Degussa BLM 112W) was charged into a 50 cc autoclave, together with 2.0 g of tetraethylammonium hydroxide as a 35 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside the autoclave. 1.2 g of ADN was injected into the autoclave and 35 ml of liquid ammonia was added. The mixture was heated to 80° C. , and reacted with hydrogen at a total pressure of 1000 psig (7.00 MPa). After 35 minutes the yield of 6-aminocapronitrile reached ca. 80% at 96% ADN conversion for a selectivity of 83%.

EXAMPLE 8

1.2 g of sponge Ni catalyst (Degussa BLM 112W) was charged into a 50 cc autoclave, together with 2.0 g of tetrapropylammonium hydroxide as a 1.0M solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1060 psig (7.41 MPa). After 25 minutes, the yield of 6-aminocapronitrile reached ca. 80% at 95% ADN conversion for a selectivity of 84%.

EXAMPLE 9

1.2 g of sponge Ni catalyst (Degussa BLM 112W) was charged into a 50cc autoclave, together with 2.0 g of tetrabutylammonium hydroxide as a 40 wt % solution in water. Subsequently, 35 ml of liquid ammonia was added, and the mixture was heated to 70° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 70° C., and reacted with hydrogen at a total pressure of 1062 psig (7.43 MPa). After 30 minutes the yield of 6-aminocapronitrile reached ca. 80% at 94% ADN conversion for a selectivity of 85%.

EXAMPLE 10

1.2 g of a 5% rhodium on alumina catalyst (obtained from Engelhard) was charged into a 50 cc autoclave, together with 2.0 g of tetrabutylammonium hydroxide as a 40 wt % solution in water. Subsequently 35 cc of liquid ammonia was added, and the mixture was heated to 80° C. with stirring. The pressure was adjusted to 1000 psig (7.00 MPa) with hydrogen, then kept under such conditions for 1.0 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1062 psig (7.43 MPa). After 75 minutes the yield of 6-aminocapronitrile reached 82% at 98% ADN conversion for a selectivity of 84%.

EXAMPLE 11

5.0 g of Raney® Co was charged into a 50 cc autoclave, together with 2.0 g of tetrabutylammonium hydroxide as a 40 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hour. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1062 psig (7.43 MPa). After 30 minutes the yield of 6-aminocapronitrile reached 71% at 94% ADN conversion for a selectivity of 76%.

EXAMPLE 12

0.3 g of sponge Ni catalyst (Degussa BLM 112W) was charged into a 50 cc autoclave, together with 0.5 g of tetrabutylammonium hydroxide as a 40 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1062 psig (7.43 MPa). After 40 minutes the yield of 6-aminocapronitrile reached ca. 73% at 92% ADN conversion for a selectivity of 79%.

EXAMPLE 13

A 50 cc autoclave was charged with 3.2 g of ADN, 1.2 g of sponge Ni catalyst (Degussa BLM 112W) and 0.5 g of tetrabutylphosphonium hydroxide as a 40 wt % solution in water. Subsequently, 35 ml of liquid ammonia was added, the mixture was heated to 80° C., and reacted with hydrogen at a total pressure of 1051 psig (7.35 MPa). After 6 minutes the yield of 6-aminocapronitrile reached ca. 72% at 90% ADN conversion for a selectivity of 80%.

EXAMPLE 14

1.2 g of sponge Ni catalyst (Degussa BLM 112W) was charged into a 50 cc autoclave, together with 2.0 g of tetrabutylphosphonium hydroxide as a 40 wt % solution in water. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1055 psig (7.38 MPa). After 10 minutes the yield of 6-aminocapronitrile reached ca. 74% at 92% ADN conversion for a selectivity of 80%.

EXAMPLE 15

5.0 g of sponge Ni catalyst (obtained from Activated Metals Corp. (Sevierville, Tenn.), Catalog No. A4000) was charged into a 50 ml autoclave, together with 0.08 g of iron nonacarbonyl—$Fe_2(CO)_9$. Subsequently, 35 ml of liquid ammonia was added, and the mixture was heated to 80° C. with stirring; the pressure was adjusted to 1000 psig (7.00 MPa) with hydrogen, then kept under such conditions for 5 hrs. After cooling, the pressure was released and the sample was transferred to a dry box, washed with deaerated methanol, and stored under anaerobic conditions. 1.2 g of the sponge Ni catalyst, pretreated with iron nonacarbonyl—$Fe_2(CO)_9$, as described above, was charged into the autoclave together with 3.2 g of ADN and 35 ml of liquid ammonia, heated to 80° C., and reacted with hydrogen at a total pressure of 1000 psig (7.00 MPa). After 100 minutes the yield of 6-aminocapronitrile reached ca. 77% at 92% ADN conversion for a selectivity of 82%.

EXAMPLE 16

5.0 g of sponge Ni catalyst (obtained from Activated Metals Corp. (Sevierville, Tenn.), Catalog No. A4000) was charged into a 50 ml autoclave, together with 0.08 g of hexarhodium hexadecacarbonyl—$Rh_6(CO)_{16}$. Subsequently, 35 ml of liquid ammonia was added, and the mixture was heated to 80° C. with stirring; the pressure was adjusted to 1000 psig (7.00 MPa) with hydrogen, then kept under such conditions for 5 hrs. After cooling, the pressure was released and the sample was transferred to a dry box, washed with deaerated methanol, and stored under anaerobic conditions. 1.2 g of the sponge Ni catalyst, pretreated with hexarhodium hexadecacarbonyl—$Rh_6(CO)_{16}$, as described above, was charged into the autoclave together with 3.2 g of ADN and 35 ml of liquid ammonia, heated to 80° C., and reacted with hydrogen at a total pressure of 1000 psig (7.00 MPa). After 40 minutes the yield of 6-aminocapronitrile reached ca. 72% at 89% ADN conversion for a selectivity of 81%.

EXAMPLE 17

5.0 g of sponge Ni catalyst (obtained from Activated Metals Corp. (Sevierville, Tenn.), Catalog No. A4000) was charged into a 50ml autoclave, together with 0.12 g of osmium carbonyl. Subsequently, 35 ml of liquid ammonia was added, and the mixture was heated to 80° C. with stirring; the pressure was adjusted to 1000 psig (7.00 MPa) with hydrogen, then kept under such conditions for 3 hrs. After cooling, the pressure was released and the sample was transferred to a dry box, washed with deaerated methanol, and stored under anaerobic conditions. 1.2 g of the sponge Ni catalyst, pretreated with osmium carbonyl, as described above, was charged into the autoclave together with 3.2 g of ADN and 35 ml of liquid ammonia, heated to 80° C., and reacted with hydrogen at a total pressure of 1000 psig (7.00 MPa). After 180 minutes the yield of 6-aminocapronitrile reached ca. 76% at 93% ADN conversion for a selectivity of 82%.

EXAMPLE 18

0.75 g of the sponge Ni catalyst, pretreated with osmium carbonyl, as described in Example 3, was charged into the autoclave together with 2.0 g of ADN and 35 ml of liquid ammonia, heated to 80° C., and reacted with hydrogen at a total pressure of 1000 psig (7.00 MPa). After 30 minutes the yield of 6-aminocapronitrile reached ca. 73% at 83% ADN conversion for a selectivity of 88%.

EXAMPLE 19

5.0 g of sponge Ni catalyst (obtained from Activated Metals Corp. (Sevierville, Tenn.), Catalog No. A4000) was charged into a 50 ml autoclave, together with 0.08 g of ruthenium carbonyl. Subsequently, 35 ml of liquid ammonia was added, and the mixture was heated to 80° C. with stirring; the pressure was adjusted to 1000 psig (7.00 MPa) with hydrogen, then kept under such conditions for 3 hrs. After cooling, the pressure was released and the sample was transferred to a dry box, washed with deaerated methanol, and stored under anaerobic conditions. 1.2 g of the sponge Ni catalyst, pretreated with ruthenium carbonyl, as described above, was charged into the autoclave together with 3.2 g of ADN and 35 ml of liquid ammonia, heated to 80° C., and reacted with hydrogen at a total pressure of 1000 psig (7.00 MPa). After 60 minutes the yield of 6-aminocapronitrile reached ca. 76% at 91% ADN conversion for a selectivity of 84%.

EXAMPLE 20

A 50 ml autoclave was charged with 3.2 g of ADN, 1.2 g of sponge Ni catalyst (obtained from Activated Metals Corp. (Sevierville, Tenn.), Catalog No. A4000), 0.25 g of NaOH, 0.25 g of $H_2O$, 32 ml of MeOH and 0.19 g of ruthenium carbonyl—$Ru_3(CO)_{12}$. The mixture was heated to 70° C., then brought in contact with hydrogen for a total pressure of 1000 psig (7.00 MPa), and run for 3 hours. After 180 minutes the yield of 6-aminocapronitrile reached ca. 71% at 92% ADN conversion for a selectivity of 77%.

EXAMPLE 21

A 50 ml autoclave was charged with 3.2 g of ADN, 1.2 g of sponge Ni catalyst (obtained from Activated Metals Corp. (Sevierville, Tenn.), Catalog No. A4000), 0.25 g of NaOH, 0.25 g of $H_2O$, 35 ml of MeOH and 0.2 g of ruthenium carbonyl—$Ru_3(CO)_{12}$. The mixture was heated to 70° C., then brought in contact with hydrogen for a total pressure of 500 psig (3.5 MPa), and run for 8 hours. After 8 hours the yield of 6-aminocapronitrile reached ca. 71% at 88% ADN conversion for a selectivity of 81%.

EXAMPLE 22

A 50 ml autoclave was charged with 3.2 g of ADN, 1.2 g of sponge Ni catalyst (obtained from Activated Metals Corp. (Sevierville, Tenn.), Catalog No. A4000), 0.25 g of NaOH, 0.25 g of $H_2O$, 35 ml of MeOH and 0.1 g of iron nonacarbonyl—$Fe_2(CO)_9$. The mixture was heated to 70° C., then brought in contact with hydrogen for a total pressure of 500 psig (3.5 MPa), and run for 7 hours. After 7 hours the yield of 6-aminocapronitrile reached ca. 74% at 86% ADN conversion for a selectivity of 86%.

EXAMPLE 23

A 50 ml autoclave was charged with 3.2 g of ADN, 1.2 g of sponge Ni catalyst (obtained from Activated Metals Corp. (Sevierville, Tenn.), Catalog No. A4000), 0.25 g of NaOH, 0.25 g of $H_2O$, 35 ml of MeOH and 0.07 g of iron nonacarbonyl. The mixture was heated to 70° C., then brought in contact with hydrogen for a total pressure of 500 psig (3.5 MPa), and run for 5 hours. After 4 hours the yield of 6-aminocapronitrile reached ca. 75% at 93% ADN conversion for a selectivity of 81%.

EXAMPLE 24

A 50 ml autoclave was charged with 3.2 g of ADN, 1.2 g of sponge Ni catalyst (obtained from Activated Metals Corp. (Sevierville, tenn.), Catalog No. A4000), 0.25 g of NaOH, 0.25 g of $H_2O$, 35 ml of MeOH and 0.05 g of iron nonacarbonyl. The mixture was heated to 70° C., then brought in contact with hydrogen for a total pressure of 500 psig (3.5 MPa), and run for 3 hours. After 90 minutes the yield of 6-aminocapronitrile reached ca. 73% at 95% ADN conversion for a selectivity of 77%.

EXAMPLE 25

5.0 g of sponge Ni catalyst (Activated metals A4000) was charged into a 50 cc autoclave, together with 0.7 g of tert.-octyl isonitrile. Subsequently, 35 ml of liquid ammonia was added, and the mixture was heated to 80° C. with stirring. The pressure was adjusted to 1000 psig (7.00 MPa) with hydrogen, and the autoclave was kept under such conditions for 3 hrs. After cooling, the pressure was released and the sample was transferred to a dry box, washed with deaerated methanol, and stored under anaerobic conditions. A portion (1.2 g) of the sponge Ni catalyst, pretreated with tert-octyl isonitrile as described above, was charged into the autoclave together with 3.2 g of ADN and 35 ml of liquid ammonia, heated to 60° C., and reacted with hydrogen at a total pressure of 1000 psig (7.00 MPa). After 20 minutes the yield of 6-aminocapronitrile reached ca. 72% at 89% ADN conversion for a selectivity of 81%.

EXAMPLE 26

5.0 g of sponge Ni catalyst (Degussa BLM 112W) was charged into a 50 cc autoclave, together with 5.0 g of tert.-butyl isonitrile. Subsequently, 30 ml of liquid ammonia was added, and the mixture was heated to 80° C. with stirring. The pressure was adjusted to 919 psig (6.44 MPa) with hydrogen, and the autoclave was kept under such conditions for 4.5 hrs. After cooling, the pressure was released and the sample was transferred to a dry box, washed with deaerated methanol, and stored under anaerobic conditions. A portion (1.2 g) of the sponge Ni catalyst, pretreated with tert-butyl isonitrile as described above, was charged into the autoclave together with 3.2 g of ADN and 35 ml of liquid ammonia, heated to 60° C., and reacted with hydrogen at a total pressure of 912 psig (6.39 MPa). After 100 minutes the yield of 6-aminocapronitrile reached ca. 70% at 92% ADN conversion for a selectivity of 76%.

EXAMPLE 27

1.2 g of the sponge Ni catalyst, pretreated with tert-butyl isonitrile, as described in Example 2, was charged into the autoclave together with 3.2 g of ADN and 35 ml of liquid ammonia, heated to 70° C., and reacted with hydrogen at a total pressure of 883 psig (6.19 MPa). After 50 minutes the yield of 6-aminocapronitrile reached ca. 70% at 85% ADN conversion for a selectivity of 82%.

EXAMPLE 28

2.5 g of sponge Ni catalyst (Degussa BLM 112W) was charged into a 50 cc autoclave, together with 2.5 g of iso-propyl isonitrile. Subsequently, 35 ml of liquid ammonia was added, and the mixture was heated to 80° C. with stirring. The pressure was adjusted to 990 psig (6.93 MPa) with hydrogen, and the autoclave was kept under such conditions for 3 hrs. After cooling, the pressure was released and the sample was transferred to a dry box, washed with deaerated methanol, and stored under anaerobic conditions. A portion (0.6 g) of the sponge Ni catalyst, pretreated with isopropyl isonitrile as described above, was charged into the autoclave together with 3.2 g of ADN and 35 ml of liquid ammonia, heated to 40° C., and reacted with hydrogen at a total pressure of 990 psig (6.93 MPa). After 4 hours the yield of 6-aminocapronitrile reached ca. 69% at 88% ADN conversion for a selectivity of 78%.

EXAMPLE 29

5.0 g of sponge Ni catalyst (Degussa BLM 112W) was charged into a 50 cc autoclave, together with 2.5 g of n-butyl isonitrile. Subsequently, 35 ml of liquid ammonia was added, and the mixture was heated to 40° C. with stirring. The pressure was adjusted to 985 psig (6.90 MPa) with hydrogen, and the autoclave was kept under such conditions for 7 hrs. After cooling, the pressure was released and the sample was transferred to a dry box, washed with deaerated methanol, and stored under anaerobic conditions. A portion (1.2 g) of the sponge Ni catalyst, pretreated with n-butyl isonitrile as described above, was charged into the autoclave together with 3.2 g of ADN and 35 ml of liquid ammonia, heated to 40° C., and reacted with hydrogen at a total pressure of 1014 psig (7.10 MPa). After 60 minutes the yield of 6-aminocapronitrile reached ca. 69% at 89% ADN conversion for a selectivity of 78%.

EXAMPLE 30

5.0 g of Raney® Co was charged into a 50 cc autoclave, together with 2.5 g of n-butyl isonitrile. Subsequently, 35 ml of liquid ammonia was added, and the mixture was heated to 80° C. with stirring. The pressure was adjusted to 902 psig (6.32 MPa) with hydrogen, and the autoclave was kept under such conditions for 2.5 hrs. After cooling, the pressure was released and the sample was transferred to a dry box, washed with deaerated methanol, and stored under anaerobic conditions. A portion (1.2 g) of the Raney® Co catalyst, pretreated with n-butyl isonitrile as described above, was charged into the autoclave together with 3.2 g of ADN and 35 ml of liquid ammonia, heated to 40° C., and reacted with hydrogen at a total pressure of 946 psig (6.63 MPa). After 105 minutes the yield of 6-aminocapronitrile reached ca. 64% at 86% ADN conversion for a selectivity of 74%.

EXAMPLE 31

A 50 cc autoclave was charged with 3.2 g of ADN, 0.6 g of Ni on MgO, 0.25 g of NaOH, 0.25 g of $H_2O$, 35 ml of MeOH and 0.5 g of benzyl isonitrile. The mixture was heated to 70° C., then brought in contact with hydrogen for a total pressure of 524 psig (3.72 MPa), and run for 1 hour. After 10 minutes the yield of 6-aminocapronitrile reached ca. 64% at 86% ADN conversion for a selectivity of 74%.

EXAMPLE 32

1.2 g of a 5% rhodium on alumina catalyst (obtained from Engelhard) was charged into a 50 cc autoclave, together with 0.30 g of tetrabutylammonium cyanide ($Bu_4NCN$). Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 3.2 g of ADN was injected into the autoclave and 35 ml of liquid ammonia was added. The mixture was heated to 80° C., and reacted with hydrogen at a total pressure of 1000 psig (7.00 MPa). After 120 minutes, the yield of 6-aminocapronitrile reached ca. 85% at 97% ADN conversion for a selectivity of 88%.

EXAMPLE 33

1.2 g of sponge Ni catalyst was charged into a 50 cc autoclave, together with 0.25 g of tetrabutylammonium cyanide ($Bu_4NCN$). Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 3.2 g of ADN was injected into the autoclave and 35 ml of liquid ammonia was added. The mixture was heated to 80° C., and reacted with hydrogen at a total pressure of 1000 psig (7.00 MPa). After 160 minutes the yield of 6-aminocapronitrile reached ca. 83% at 95% ADN conversion for a selectivity of 87%.

EXAMPLE 34

1.2 g of sponge Ni catalyst was charged into a 50 cc autoclave, together with 0.25 g of tetrabutylammonium cyanide ($Bu_4NCN$). Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 9.6 g of ADN was injected into the autoclave and 30 ml of liquid ammonia was added. The mixture was heated to 80° C., and reacted with hydrogen at a total pressure of 1000 psig (7.00 MPa). After 220 minutes, the yield of 6-aminocapronitrile reached ca. 80% at 96% ADN conversion for a selectivity of 83%.

EXAMPLE 35

1.2 g of Raney® Co was charged into a 50 cc autoclave, together with 0.25 g of tetrabutylammonium cyanide (Bu$_4$NCN). Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 9.6 g of ADN was injected into the autoclave and 30 ml of liquid ammonia was added. The mixture was heated to 80° C., and reacted with hydrogen at a total pressure of 1000 psig (7.00 MPa). After 135 minutes the yield of 6-aminocapronitrile reached ca. 72% at 94% ADN conversion for a selectivity of 77%.

EXAMPLE 36

1.2 g of a catalyst prepared by the basic leaching of an alloy containing Al 54 wt %, Ni 23 wt %, Co 23 wt % and Cr 1 wt %, was charged into a 50 cc autoclave, together with 0.25 g of tetrabutylammonium cyanide (Bu$_4$NCN). Subsequently, 35 ml of liquid ammonia was added, and the mixture was heated to 80° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 3.2 g of ADN was injected into the autoclave and 30 ml of liquid ammonia was added. The mixture was heated to 80° C., and reacted with hydrogen at a total pressure of 1000 psig (7.00 MPa). After 260 minutes, the yield of 6-aminocapronitrile reached ca. 82% at 97% ADN conversion for a selectivity of 85%.

EXAMPLE 37

1.2 g of sponge Ni catalyst was charged into a 50 cc autoclave, together with 3.2 g of ADN and 0.018 g of LiCN as a 0.5 M solution in dimethyl formamide. Subsequently, 35 ml of liquid ammonia was added, and the mixture was heated to 80° C. with stirring. The pressure was adjusted to 1000 psig (7.00 MPa) with hydrogen. After 200 minutes, the yield of 6-aminocapronitrile reached ca. 76% at 91% ADN conversion for a selectivity of 84%.

EXAMPLE 38

1.2 g of sponge Ni catalyst was charged into a 50 cc autoclave, together with 3.2 g of ADN and 0.03 g of NaCN. Subsequently, 35 ml of liquid ammonia was added, and the mixture was heated to 80° C. with stirring. The pressure was adjusted to 1000 psig (7.00 MPa) with hydrogen. After 330 minutes, the yield of 6-aminocapronitrile reached ca. 77% at 94% ADN conversion for a selectivity of 82%.

EXAMPLE 39

1.2 g of Raney® cobalt was charged into a 50 cc autoclave, together with 3.2 g of ADN and 0.03 g of NaCN. Subsequently, 35 ml of liquid ammonia was added, and the mixture was heated to 80° C. with stirring. The pressure was adjusted to 1000 psig (7.00 MPa) with hydrogen. After 570 minutes, the yield of 6-aminocapronitrile reached ca. 71% at 96% ADN conversion for a selectivity of 74%.

EXAMPLE 40

1.2 g of sponge Ni catalyst was charged into a 50 cc autoclave, together with 0.25 g of tetrabutylammonium cyanide (Bu$_4$NCN). Subsequently, 35 ml of liquid ammonia was added, and the mixture was heated to 70° C. with stirring. The pressure was adjusted to 1000 psig (7.00 MPa) with hydrogen, and the autoclave was kept under such conditions for 1 hr. After cooling, the liquid phase was filtered off, leaving the pretreated catalyst inside of the autoclave. 9.6 g of ADN was injected into the autoclave and 35 ml of liquid ammonia was added. The mixture was heated to 70° C., and reacted with hydrogen at a total pressure of 1000 psig (7.00 MPa). After 240 minutes the yield of 6-aminocapronitrile reached ca. 82% at 94% A conversion for a selectivity of 87%.

EXAMPLE 41

1.2 g of sponge Ni catalyst was charged into a 50 cc autoclave, together with 3.2 g of ADN and 0.036 ml of hydrogen cyanide. Subsequently, 35 ml of liquid ammonia was added, and the mixture was heated to 70° C. with stirring. The pressure was adjusted to 1060 psig (7.41 MPa) with hydrogen. After 180 minutes the yield of 6-aminocapronitrile reached ca. 73% at 90% ADN conversion for a selectivity of 81%.

EXAMPLE 42

1.2 g of sponge Ni catalyst was charged into a 50 cc autoclave, together with 3.2 g of ADN and 0.1 g of trimethylsilyl cyanide. Subsequently, 35 ml of liquid ammonia was added, and the mixture was heated to 80° C. with stirring. The pressure was adjusted to 1054 psig (7.37 MPa) with hydrogen. After 100 minutes the yield of 6-aminocapronitrile reached ca. 70% at 90% ADN conversion for a selectivity of 78%.

EXAMPLE 43

1.2 g of sponge Ni catalyst was charged into a 50 cc autoclave, together with 0.25 g of tetraethylammonium cyanide (Et$_4$NCN). Subsequently, 35 ml of liquid ammonia was added, and the mixture was heated to 80° C. with stirring. The pressure was adjusted to 1057 psig (7.39 MPa) with hydrogen, and the autoclave was kept under such conditions for 1 hr. After cooling, the liquid phase was filtered off, leaving the pretreated catalyst inside of the autoclave. 3.2 g of ADN was injected into the autoclave and 35 ml of liquid ammonia was added. The mixture was heated to 90° C., and reacted with hydrogen at a total pressure of 1054 psig (7.37 MPa). After 260 minutes the yield of 6-aminocapronitrile reached ca. 84W at 94% ADN conversion for a selectivity of 89%.

EXAMPLE 44

1.2 g of sponge Ni catalyst was charged into a 50 cc autoclave, together with 0.03 g of tetraethylammonium thiocyanide (Et$_4$NSCN). Subsequently 35 ml of liquid ammonia was added, and the mixture was heated to 80° C. with stirring. The pressure was adjusted to 1000 psig (7.00 MPa) with hydrogen, then kept under such conditions for 0.5 hrs. After cooling, the liquid phase was filtered off, leaving the retreated catalyst inside of the autoclave. 1.2 g of ADN was injected into the autoclave and 35 ml of liquid ammonia was added. The mixture was heated to 80° C., and reacted with hydrogen at a total pressure of 1000 psig (7.00 MPa). After 5.4 hours the yield of 6-aminocapronitrile reached 81% at 96% ADN conversion for a selectivity of 84%.

EXAMPLE 45

1.2 g of sponge Ni catalyst was charged into a 50 cc autoclave, together with 0.05 g of tetrabutylammonium thiocyanide ($Bu_4NSCN$). Subsequently 35 ml of liquid ammonia was added, and the mixture was heated to 80° C. with stirring. The pressure was adjusted to 1000 psig (7.00 MPa) with hydrogen, then kept under such conditions for 1.0 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1000 psig (7.00 MPa). After 2.5 hours the yield of 6-aminocapronitrile reached 81% at 95% ADN conversion for a selectivity of 85%.

EXAMPLE 46

1.2 g of sponge Ni catalyst was charged into a 50 cc autoclave, together with 3.2 g of ADN and 0.1 g of tetrabutylammonium thiocyanide ($Bu_4NSCN$). Subsequently 35 cc of liquid ammonia was added, and the mixture was heated to 80° C. with stirring. The pressure was adjusted to 1044 psig (7.30 MPa) with hydrogen. After 6 hours the yield of 6-aminocapronitrile reached 80% at 95% ADN conversion for a selectivity of 84%.

EXAMPLE 47

1.2 g of Raney® Co was charged into a 50 cc autoclave, together with 0.05 g of tetraethylammonium thiocyanide ($Et_4NSCN$), Subsequently 35 cc of liquid ammonia was added, and the mixture was heated to 80° C. with stirring. The pressure was adjusted to 1000 psig (7.00 MPa) with hydrogen, then kept under such conditions for 0.5 hrs. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1024 psig (7.17 MPa). After 22 hours the yield of 6-aminocapronitrile reached 81% at 97% ADN conversion for a selectivity of 84%.

EXAMPLE 48

1.2 g of a 5% rhodium on alumina catalyst (obtained from Engelhard) was charged into a 50 cc autoclave, together with 0.012 g of tetraethylammonium thiocyanide ($Et_4NSCN$). Subsequently 35 cc of liquid ammonia was added, and the mixture was heated to 80° C. with stirring. The pressure was adjusted to 1000 psig (7.00 MPa) with hydrogen, then kept under such conditions for 1.0 hr. After cooling, the liquid phase was filtered off, leaving the pretreated catalyst inside of the autoclave. 1.2 g of ADN was injected into the autoclave and 35 ml of liquid ammonia was added. The mixture was heated to 800C, and reacted with hydrogen at a total pressure of 1052 psig (7.36 MPa). After 2.5 hours the yield of 6-aminocapronitrile reached 78% at 95% ADN conversion for a selectivity of 82%.

EXAMPLE 49

1.2 g of sponge Ni catalyst was charged into a 50 cc autoclave, together with 0.5 g of tetraethylammonium fluoride hydrate. Subsequently 35 cc of liquid ammonia was added, and the mixture was heated to 80° C. with stirring; the pressure was adjusted to 1000 psig (7.00 MPa) with hydrogen, then kept under such conditions for 1.0 hrs. After cooling, the liquid phase was filtered off, leaving the pretreated catalyst inside of the autoclave. 3.2 g of ADN was injected into the autoclave and 35 ml of liquid ammonia was added, the mixture was heated to 70° C., and reacted with hydrogen at a total pressure of 1000 psig (7.00 MPa). After 45 minutes the yield of 6-aminocapronitrile reached ca. 83% at 96% ADN conversion for a selectivity of 86%.

EXAMPLE 50

1.2 g of sponge Ni catalyst and 3.2 g of ADN were charged into a 50 cc autoclave, together with 0.3g of tetraethylammonium fluoride hydrate. Subsequently 35 cc of liquid ammonia was added, and the mixture was heated to 80° C. with stirring and reacted with hydrogen at a total pressure of 1044 psig (7.30 MPa). After 20 minutes the yield of 6-aminocapronitrile reached ca. 79% at 98% ADN conversion for a selectivity of 81%.

EXAMPLE 51

1.2 g of sponge Ni catalyst was charged into a 50 cc autoclave, together with 1.0 g of tetraethylammonium fluoride hydrate. Subsequently 35 cc of liquid ammonia was added, and the mixture was heated to 80° C. with stirring; the pressure was adjusted to 1000 psig (7.00 MPa) with hydrogen, then kept under such conditions for 1.0 hrs. After cooling, the liquid phase was filtered off, leaving the pretreated catalyst inside of the autoclave. 3.2 g of ADN was injected into the autoclave and 35 ml of liquid ammonia was added, the mixture was heated to 70° C., and reacted with hydrogen at a total pressure of 1047 psi (7.32 MPa). After 55 minutes the yield of 6-aminocapronitrile reached ca. 78% at 97% ADN conversion for a selectivity of 80%.

EXAMPLE 52

1.2 g of Raney® Co was charged into a 50 cc autoclave, together with 2.0 g of tetraethylammonium fluoride hydrate. Subsequently 35 cc of liquid ammonia was added, and the mixture was heated to 80° C. with stirring; the pressure was adjusted to 1000 psig (7.00 MPa) with hydrogen, then kept under such conditions for 1.0 hrs. After cooling, the liquid phase was filtered off, leaving the pretreated catalyst inside of the autoclave. 3.2 g of ADN was injected into the autoclave and 35 ml of liquid ammonia was added, the mixture was heated to 70° C., and reacted with hydrogen at a total pressure of 1000 psig (7.00 MPa). After 16 minutes the yield of 6-aminocapronitrile reached ca. 74% at 94% ADN conversion for a selectivity of 79%.

EXAMPLE 53

1.2 g of $Rh(5\%)/Al_2O_3$ was charged into a 50 cc autoclave, together with 0.5 g of tetraethylammonium fluoride hydrate. Subsequently 35 cc of liquid ammonia was added, and the mixture was heated to 80° C. with stirring; the pressure was adjusted to 1000 psig (7.00 MPa) with hydrogen, then kept under such conditions for 1.0 hrs. After cooling, the liquid phase was filtered off, leaving the pretreated catalyst inside of the autoclave. 3.2 g of ADN was injected into the autoclave and 35 ml of liquid ammonia was added, the mixture was heated to 70° C., and reacted with hydrogen at a total pressure of 1000 psig (7.00 MPa). After 40 minutes the yield of 6-aminocapronitrile reached ca. 76% at 94% ADN conversion for a selectivity of 81%.

The results of the above examples are summarized in the following table:

| EX | Catalyst | Additive (Temp. ° C.) | Time | Yield | Conv | Select |
|---|---|---|---|---|---|---|
| C1 | Sponge Ni | None (60) | 30 m | 57% | 90% | 63% |
| C2 | Raney ® Co | None (70) | 40 m | 58% | 90% | 64% |
| C3 | Rh/Al$_2$O$_3$ | None (80) | 30 m | 3% | 96% | — |
| 1 | Sponge Ni | CO (60) | 75 m | 72% | 94% | 77% |
| 2 | Sponge Ni | CO (40) | 180 m | 72% | 93% | 77% |
| 3 | Raney ® Ni | CO (70) | 4.5 h | 63% | 78% | 81% |
| 4 | Raney ® Co | CO (40) | 160 m | 71% | 89% | 80% |
| 5 | Raney ® Co | CO (80) | 5 h | 74% | 94% | 79% |
| 6 | Sponge Ni | TMAOHP (80) | 24 m | 79% | 97% | 81% |
| 7 | Sponye Ni | TEAOH (80) | 35 m | 80% | 96% | 83% |
| 8 | Sponge Ni | TPAOH (80) | 25 m | 80% | 95% | 84% |
| 9 | Sponge Ni | TBAOH (70) | 30 m | 80% | 94% | 85% |
| 10 | Rh/Al$_2$O$_3$ | TBAOH (80) | 75 m | 82% | 98% | 84% |
| 11 | Raney ® Co | TBAOH (80) | 30 m | 71% | 94% | 76% |
| 12 | Sponge Ni | TBAOH (80) | 40 m | 73% | 92% | 79% |
| 13 | Sponge Ni | TBPOH (80) | 6 m | 72% | 90% | 80% |
| 14 | Sponge Ni | TBPOH (80) | 10 m | 74% | 92% | 80% |
| 15 | Sponge Ni | Fe$_2$(CO)$_9$ (80) | 100 m | 77% | 94% | 82% |
| 16 | Sponge Ni | Rh$_6$(CO)$_{16}$ (80) | 40 m | 72% | 89% | 81% |
| 17 | Sponge Ni | Os$_3$(CO)$_{12}$ (80) | 180 m | 76% | 93% | 82% |
| 18 | Sponge Ni | Os$_3$(CO)$_{12}$ (80) | 30 m | 73% | 83% | 88% |
| 19 | Sponge Ni | Ru$_3$(CO)$_{12}$ (80) | 60 m | 76% | 91% | 84% |
| 20 | Sponge Ni | Ru$_3$(CO)$_{12}$ (70) | 180 m | 71% | 92% | 77% |
| 21 | Sponge Ni | Ru$_3$(CO)$_{12}$ (70) | 8 h | 71% | 88% | 81% |
| 22 | Sponge Ni | Fe$_2$(CO)$_9$ (70) | 7 h | 74% | 86% | 86% |
| 23 | Sponge Ni | Fe$_2$(CO)$_9$ (70) | 4 h | 75% | 93% | 81% |
| 24 | Sponge Ni | Fe$_2$(CO)$_9$ (70) | 90 m | 73% | 95% | 77% |
| 25 | Sponge Ni | t-octylIn (60) | 20 m | 72% | 89% | 81% |
| 26 | Sponge Ni | t-butylIn (60) | 100 m | 70% | 92% | 76% |
| 27 | Sponge Ni | t-butylIn (70) | 50 m | 70% | 85% | 82% |
| 28 | Sponge Ni | i-propylIn (40) | 4 h | 69% | 88% | 78% |
| 29 | Sponge Ni | n-butylIn (40) | 60 m | 69% | 89% | 78% |
| 30 | Raney ® Co | n-butylIn (40) | 105 m | 64% | 86% | 74% |
| 31 | Ni/MgO | BenzylIn (70) | 10 m | 64% | 86% | 74% |
| 32 | Rh/Al$_2$O$_3$ | Bu$_4$NCN (80) | 120 m | 85% | 97% | 88% |
| 33 | Sponge Ni | Bu$_4$NCN (80) | 160 m | 83% | 95% | 87% |
| 34 | Sponge Ni | Bu$_4$NCN (80) | 220 m | 80% | 96% | 83% |
| 35 | Raney ® Co | Bu$_4$NCN (80) | 135 m | 72% | 94% | 77% |
| 36 | AlNiCoCr | Bu$_4$NCN (80) | 260 m | 82% | 97% | 85% |
| 37 | Sponge Ni | LiCN (80) | 200 m | 76% | 91% | 84% |
| 38 | Sponge Ni | NaCN (80) | 330 m | 77% | 94% | 82% |
| 39 | Raney ® Co | NaCN (80) | 570 m | 71% | 96% | 74% |
| 40 | Sponge Ni | Bu$_4$NCN (70) | 240 m | 82% | 94% | 87% |
| 41 | Sponge Ni | HCN (70) | 180 m | 73% | 90% | 81% |
| 42 | Sponge Ni | Me$_3$SiCN (80) | 100 m | 70% | 90% | 78% |
| 43 | Sponge Ni | Et$_4$NCN (90) | 260 m | 84% | 94% | 89% |
| 44 | Sponge Ni | Et$_4$NSCN (80) | 5.4 h | 81% | 96% | 84% |
| 45 | Sponge Ni | Bu$_4$NSCN (80) | 2.5 h | 81% | 95% | 85% |
| 46 | Sponge Ni | Bu$_4$NSCN (80) | 6 h | 80% | 95% | 84% |
| 47 | Raney ® Co | Et$_4$NSCN (80) | 22 h | 81% | 97% | 84% |
| 48 | Rh/Al$_2$O$_3$ | Et$_4$NSCN (80) | 2.5 h | 78% | 95% | 82% |
| 49 | Sponge Ni | TEAFH (80) | 45 m | 83% | 96% | 86% |
| 50 | Sponye Ni | TEAFH (80) | 20 m | 79% | 98% | 81% |
| 51 | Sponge Ni | TEAFH (70) | 55 m | 78% | 97% | 80% |
| 52 | Raney ® Co | TEAFH (70) | 16 m | 74% | 94% | 79% |
| 53 | Rh/Al$_2$O$_3$ | TEAFH (70) | 40 m | 76% | 94% | 81% |

We claim:

1. A process for the partial hydrogenation of a dinitrile to an aminonitrile, comprising the step of contacting the dinitrile with a hydrogen-containing fluid in the presence of (a) a solvent comprising liquid ammonia, an alcohol, or both; (b) a hydrogenation catalyst; and (c) an additive for improving the yield of and/or selectivity to the aminonitrile, wherein the dinitrile has the general formula R(CN)$_2$, wherein R is an alkylene group, and wherein the additive comprises a compound selected from the group consisting of;

carbon monoxide;

a multi-centered metal carbonyl cluster containing (i) at least two metal atoms within the cluster, (ii) at least three bridges between the metal atoms within the cluster, and (iii) at least one carbonyl group bonded to a metal atom; and an organic isonitrile.

2. The process of claim 1, wherein the dinitrile is selected from the group consisting of adiponitrile, methylglutaronitrile and alpha,omega-dodecanedinitrile.

3. The process of claim 1, wherein the solvent is liquid ammonia.

4. The process of claim 1, wherein the hydrogenation catalyst comprises a transition metal selected from the group consisting of iron, cobalt, nickel, rhodium and combinations thereof.

5. The process of claim 4, wherein the hydrogenation catalyst is in sponge metal form.

6. The process of claim 5, wherein the catalytic metal is supported on an inorganic support.

7. The process of claim 1, wherein the hydrogenation catalyst is precontacted with the additive.

8. The process of claim 1, wherein the additive is carbon monoxide.

9. The process of claim 8, wherein the ratio of carbon monoxide to hydrogenation catalyst is in the range of from about 0.001:1 to about 10:1 mmoles CO/g catalyst.

10. The process of claim 1, wherein the additive is a multi-centered metal carbonyl cluster.

11. The process of claim 10, wherein the weight ratio of additive to hydrogenation catalyst is in the range of from about 0.001:1 to about 0.5:1.

12. The process of claim 10, wherein the multi-centered metal carbonyl cluster is selected from the group consisting of Fe$_2$(CO)$_9$, Co$_4$(CO)$_{12}$, Ru$_3$(CO)$_{12}$, Rh$_6$(CO)$_{16}$, Os$_3$(CO)$_{12}$ and Ir$_4$(CO)$_{12}$, and combinations of two or more thereof.

13. The process of claim 1, wherein the additive is an organic isonitrile.

14. The process of claim 13, wherein the weight ratio of additive to hydrogenation catalyst is in the range of from about 0.001:1 to about 2:1.

15. The process of claim 13, wherein the organic isonitrile has the general formula R'—N≡C:, where R' is a hydrocarbyl group containing from 1 to 20 carbon atoms.

16. The process of claim 1, wherein the metal of the multi-centered metal carbonyl cluster is a Group VIII metal.

17. The process of claim 10, wherein the metal of the multi-centered metal carbonyl cluster is a Group VIII metal.

* * * * *